US00PP14774P2

(12) United States Plant Patent
Bourne

(10) Patent No.: US PP14,774 P2
(45) Date of Patent: May 11, 2004

(54) GRAPEVINE PLANT NAMED '13-19-30'

(50) Latin Name: *Vitis vinifera*
Varietal Denomination: 13-19-30

(75) Inventor: Timothy F. Bourne, Visalia, CA (US)

(73) Assignee: Sunview Vineyards if California, Inc., Delano, CA (US)

( * ) Notice: Subject to any disclaimer, the term of this patent is extended or adjusted under 35 U.S.C. 154(b) by 59 days.

(21) Appl. No.: 10/280,570

(22) Filed: Oct. 24, 2002

(51) Int. Cl.[7] ..... A01H 5/00
(52) U.S. Cl. ..... Plt./205
(58) Field of Search ..... Plt./205

*Primary Examiner*—Kent Bell
(74) *Attorney, Agent, or Firm*—Jondle & Associates PC

(57) ABSTRACT

This new variety of grape plant named '13-19-30' is new and different because of its very large, spherical, seedless berry and strong muscat flavor. It responds favorably to springtime applications of exogenous gibberellic acid, producing a loose, flexible cluster with a large increase in berry size over natural fruit.

2 Drawing Sheets

Genus and species: *Vitis vinifera.*

BACKGROUND AND SUMMARY OF THE INVENTION

The new grape plant named '13-19-30' is of *Vitis vinifera* parentage and resulted from a twenty year breeding program which had as its goal the development of a red, seedless, muscat-flavored table grape. The female parent (unnamed) (unpatented) resulted from a series of crosses involving 'Hunisa', 'Flame Seedless', 'Emperor', 'Thompson Seedless' and 'Nocera' (all unpatented). The male parent of the cross is an unnamed, seedless grapevine resulting from a series of crosses involving 'Emperor', 'Thompson Seedless', 'Red Muscatel' (unpatented), and 'Calmeria' (unpatented). The hybridization resulting in '13-19-30' was made near McFarland, Calif. in 1992. The seedling was selected from a population of 223 seedlings of like parentage in 1996. It was then propagated by cuttings and grafting to 'Freedom' (unpatented) rootstock in the spring of 1998 near McFarland, Calif. Those resulting plants were stable and typical of the original vine.

COMPARISON WITH PARENTAL CULTIVARS

The new grape plant named '13-19-30' somewhat resembles the cultivar 'Flame Seedless' which is one of its ancestors. However, its berries are substantially larger than those of 'Flame Seedless'. It also differs from 'Flame Seedless' by having a distinctive muscat flavor and higher sugar levels. The new variety differs from its female parent by bearing seedless berries.

DESCRIPTION OF THE FIGURES

The accompanying drawings illustrate the following.

DETAILED BOTANICAL DESCRIPTION OF THE INVENTION

Figure 1:
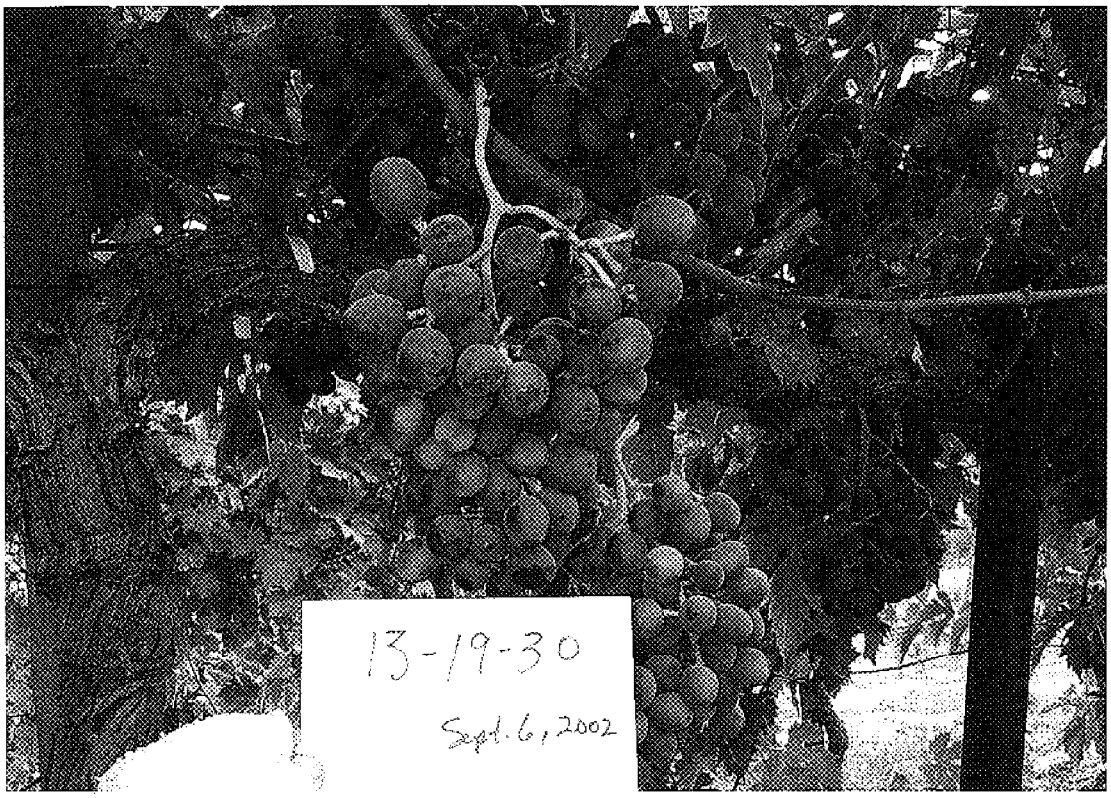
FIG. 1 shows a fruit cluster at harvest.
Figure 2:
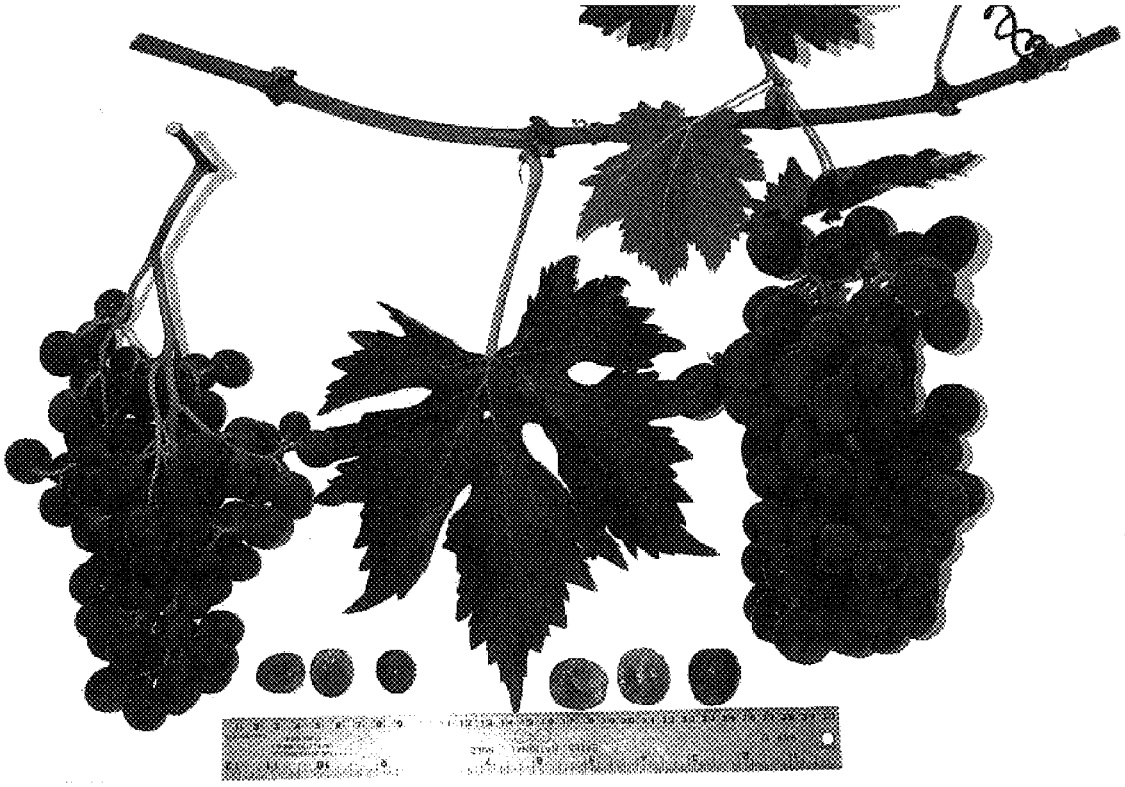
FIG. 2 shows a cane, leaf, natural fruit cluster (left) and fruit cluster following gibberellic acid applications (right).

The following description of grapevine '13-19-30' contains references to color names taken from the Munsell Color Chart for Plant Tissues, published by Munsell Color, New Windsor, N.Y. Descriptors used herein conform to those set forth by the International Board for Plant Genetic Resources Institute Grape Descriptors (Vitis spp.) of 1983 and/or 1997 which were developed in collaboration with the Office International de la Vigne et du Vin (OIV) and the International Union for the Protection of New Varieties of Plants (UPOV) and published in Descriptors for Grapevine (Vitis spp.) (Anonymous, International Plant Genetic Resources Institute, 1997, ISBN 92-9043-352-3).

Descriptions of the new invention apply to vines of '13-19-30' grown on 'Freedom' rootstock at a density of 1,537 vines per hectare grown in Kern County, Calif. in 2001. These vines were in their first year of full production having been planted in 1998. These descriptions are believed to apply generally to the new variety grown under similar circumstances elsewhere:

VINE

General:

*Vigor.*—Vines spur pruned and thinned to 32 shoots produce canes average 285 cm.
*Density of foliage.*—Moderate.
*Productivity.*—Productive when spur pruned, up to 39,630 kg./hectare.
*Hardiness.*—Observed hardiness to 0 C.
*Rootstock.*—Freedom.

Trunk:

*Shape.*—Broadly elliptical.
*Straps.*—Long, split.
*Surface texture.*—Shaggy.
*Inner bark color.*—Brown 2.5YR 4/8.
*Outer bark color.*—7.5YR 5/2.
*Trunk circumference.*—6 year old vines average15.3 at 1 meter height.

LEAVES

Mature leaves:

*Average blade length.*—17.1 cm.
*Average blade width.*—20.7 cm.
*Size of blade.*—Medium to large.
*Shape.*—Pentagonal.

*Anthocyanin coloration of main veins on the upper side of the blade.*—Slight or absent, 5R 6/10.
*Mature leaf profile.*—Flat.
*Blistering surface of blade upper surface.*—Absent.
*Leaf blade tip.*—In plane of the leaf.
*Margins.*—Lobed, serrate, undulate.
*Apex.*—Narrowly acuminate.
*Thickness.*—Medium.
*Undulation of blade between main and lateral veins.*—Slight.
*Shape of teeth.*—Conical, both sides convex.
*Length of teeth.*—Variable, 3–15 mm.
*Ratio length/width of teeth.*—About 1:1.
*General shape of petiole sinus.*—Broadly ovate.
*Tooth at petiole sinus.*—Absent.
*Petiole sinus limited by veins.*—Absent.
*Shape of upper lateral sinus.*—Closed.
*Prostrate hairs between veins on lower surface of blade.*—Absent.
*Erect hairs between hairs on lower surface of blade.*—Absent.
*Prostrate hairs on main veins on lower surface of blade.*—Absent.
*Density of erect hairs on main veins on lower surface of blade.*—Dense at vein junctions, sparse but persistent along entire length of main veins.
*Prostrate hairs on main veins on upper surface of blade.*—Absent.
*Leaf base.*—Sagittate.

Upper surface:
*Summer color.*—Dark green: 7.5 GY 4/4 to 4/6.
*Autumn color.*—Yellow: 5Y 8/10.
*Surface texture.*—Smooth.
*Surface appearance.*—Dull.
*Goffering of blade.*—Absent.

Lower surface:
*Summer color.*—Dark green: 7.5GY 5/6 to 5/8.
*Autumn color.*—Yellow, 2.5Y 8/6.
*Anthocyanin coloration of main veins on lower leaf surface.*—Absent or very slight at base of main veins, 5R 6/10.
*Glossiness.*—Low.
*Pubescence.*—Absent.
*Surface texture.*—Smooth.
*Surface appearance.*—Dull.

Petiole:
*Length of petiole.*—11.7 cm.
*Length of petiole compared to middle vein.*—Considerably shorter.
*Density of prostrate hairs on petiole.*—Absent.
*Density of erect hairs on petiole.*—Absent.
*Shape of base of petiole sinus.*—Broadly ovate.
*Diameter.*—4 mm.
*Color.*—Mostly 2.5GY 8/8 with streaks of 5R 6/10.

Tendrils:
*Number.*—At every node above node 5.
*Length.*—29.5 cm.
*Diameter.*—2 mm.
*Texture.*—Smooth.
*Color.*—2.5GY 7/8.

Canes:
*Shape.*—Broadly elliptical.
*Internode length.*—10.5 cm.
*Width at node.*—15 mm.
*Cross section.*—Circular.
*Surface.*—Smooth.
*Main color.*—Yellowish brown 7.5 6/6 to 6/8.
*Lenticels.*—Inconspicuous.
*Erect hairs on nodes.*—Absent.
*Erect hairs on internodes.*—Absent.

Laterals:
*Shape.*—Circular to broadly elliptical.
*Number.*—Laterals generally produced at all nodes above the second node.
*Length.*—8 cm.–76.2 cm.
*Diameter.*—3–6 mm.
*Internode length.*—2–12 cm.
*Color.*—10R 4/6.

Buds:
*Shape.*—Conical.
*Length.*—8 mm.
*Width.*—7 mm.
*Height.*—7 mm.
*Color.*—2.5GY 7/8.
*Cane bud fruitfulness.*—Basal buds fruitful, 1–2 clusters per shoot.

FLOWERS

General:
*Flower sex.*—Perfect.
*Position of first flowering nodes.*—$3^{rd}$ to $4^{th}$.
*Number of inflorescences per shoot.*—1 or 2.
*Pedicel length.*—3.5 mm.
*Calyptra color.*—5GY 7/8.
*Ovary length.*—2 mm.
*Ovary width.*—1.5 mm.
*Ovary color.*—5GY 4/8.
*Filament length.*—2 mm.
*Filament color.*—2.5GY 8/2.
*Anther length.*—1 mm.
*Anther colot.*—2.5GY 8/8.
*Date of full bloom.*—May 15, 2001 in McFarland, Calif.
*Time of bloom.*—Mar. 22, 2003.

FRUIT

General:
*Ripening period.*—Mid-season at Delano, Calif.; about 1 week after 'Thompson Seedless'.
*Date of ripening.*—Aug. 25, 2001.
*Use.*—Fresh market.
*Keeping quality.*—Very good.
*Resistance.*—Insects: typical of *Vitis vinifera*. Diseases: typical of *Vitis vinifera*.
*Shipping quality.*—Good.
*Date of first harvest.*—Aug. 25, 2001.
*Solids-sugar.*—High, about 20 brix at full maturity.
*Refractometer test.*—21.0 brix.

Cluster:
*Bunch size.*—Medium.
*Bunch length (peduncle excluded).*—About 26.0 cm.
*Bunch width.*—About 17.3 cm.
*Bunch weight (natural).*—476 g.
*Bunch weight (gibberellic acid treated).*—857 g.
*Bunch density.*—Loose.
*Number of berries.*—175.
*Form.*—Conical.

Peduncle:
*Length of peduncle.*—3.5 cm.
*Lignification of peduncle.*—Medium.
*Color.*—2.5YR 4/6.

Berry:

*Size.*—Medium.

*Uniformity of size.*—Uniform.

*Berry weight* (*natural*).—5.2 g.

*Berry weight* (*gibberellic acid treated*).—8.9 g.

*Shape.*—Spherical.

*Presence of seeds.*—Seedless; most berries develop 1 or 2 small, soft rudimentary seeds 1–2 mm in length. Seeds are red in color, 2.5R 4/10.

*Cross section.*—Circular.

*Dimensions.*—Longitudinal axis about 2.5 cm.; horizontal axis about 2.3 cm.

*Skin color* (*without bloom*).—Red: 5R 3/8 to 3/10.

*Coloration of flesh.*—Translucent, 7.5GY 8/2.

*Juiciness of flesh.*—Very juicy.

*Berry firmness.*—Firm.

*Particular flavor.*—Muscat.

*Bloom* (*cuticular wax*).—Strong.

*Pedicel length.*—12 mm.

*Berry separation from pedicel.*—Moderate.

Skin:

*Thickness.*—Medium.

*Texture.*—Tender.

*Reticulation.*—Absent.

*Roughness.*—Absent.

*Tenacity.*—Tenacious to flesh.

*Tendency to crack.*—Resistant.

What is claimed is:

1. A new and distinct variety of grape plant named '13-19-30' as herein illustrated and described.

* * * * *

MZI Selection 13-19-30